United States Patent
Beyerle et al.

[11] 3,959,281
[45] May 25, 1976

[54] PIPERAZINO SUBSTITUTED COUMARIN DERIVATIVES

[75] Inventors: Rudi Beyerle, Bruchköbel, Germany; Adolf Stachel, deceased, late of Germany; Ingeburg Lydia Katharina Stachel, heiress, Frankfurt am Main-Fechenheim, Germany; Rolf-Eberhard Nitz, Bergen-Enkheim, Germany; Klaus Resag; Eckhard Schraven, both of Frankfurt am Main-Fechenheim, Germany

[73] Assignee: Cassella Farbwerke Mainkur Aktiengesellschaft, Frankfurt am Main-Fechenheim, Germany

[22] Filed: July 27, 1971

[21] Appl. No.: 166,600

Related U.S. Application Data

[62] Division of Ser. No. 789,919, Jan. 8, 1969, Pat. No. 3,652,557.

[30] Foreign Application Priority Data

Jan. 19, 1968   Germany............................ 1668877

[52] U.S. Cl............................ 260/268 BC; 424/250
[51] Int. Cl.²................ C07D 405/10; C07D 405/06
[58] Field of Search................ 260/268 BC, 345.2 R

[56]  References Cited
UNITED STATES PATENTS

| | | | |
|---|---|---|---|
| 3,538,098 | 11/1970 | Beterle et al. ................ | 260/268 BC |
| 3,652,557 | 3/1972 | Beyerle et al.................. | 260/268 BC |

Primary Examiner—Alton D. Rollins
Assistant Examiner—Jose Tovar
Attorney, Agent, or Firm—Francis M. Crawford

[57]     ABSTRACT

The present invention relates to new coumarin compounds useful as coronary dilators and having the formula

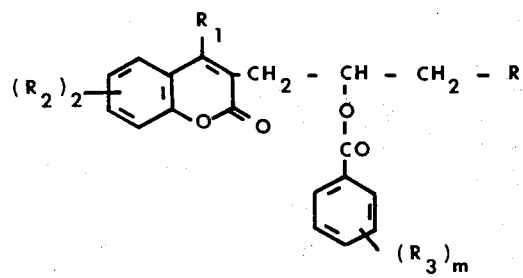

or the hydrochloric acid addition salts thereof, and to methods of preparing same either by acylating, in the presence of acid-binding agents, if desired, coumarin derivatives having the formula

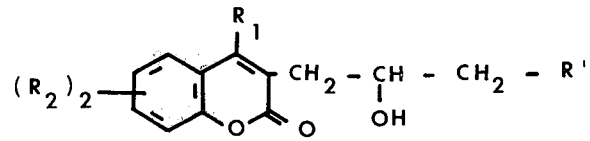

with acylating agents selected from the group consisting of alkoxybenzoic acid having the formula

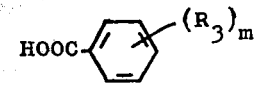

and functional derivatives thereof, or by condensing, in the presence of acid-binding agents, if desired, coumarin derivatives having the formula

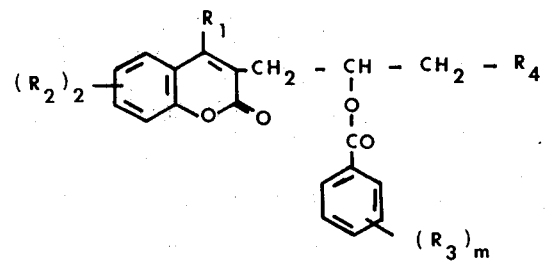

with an amine having the formula RH, wherein R is piperazino which is free of acyloxy groups and is bound via a nitrogen atom; $R_1$ is selected from the group consisting of alkyl radicals having 1–4 carbon atoms and phenyl; $R_2$ is selected from the group consisting of 5,7-, 6,7- and 7,8-positioned alkoxy groups having 1–4 carbon atoms; $R_3$ is selected from alkoxy groups having 1–4 carbon atoms; $R_4$ is selected from the group consisting of chlorine and bromine; R' is piperazino which is free of hydroxy groups and is bound via a nitrogen group; and m is selected from the group consisting of 1, 2, and 3.

6 Claims, No Drawings

PIPERAZINO SUBSTITUTED COUMARIN DERIVATIVES

The present application is a division of our U.S. Ser. No. 789,919, filed Jan. 8, 1969, now U.S. Pat. No. 3,652,557, issued Mar. 28, 1972.

The present application relates to new pharmacologically valuable, basically substituted coumarin compounds having the formula

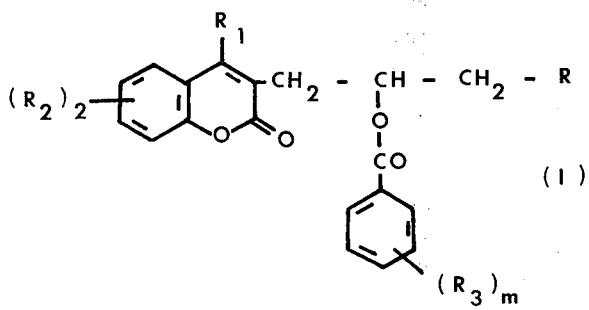

or the hydrochloric acid addition salts thereof, wherein
R is piperazino, which is free of acyloxy groups and is bound via a nitrogen atom;
$R_1$ is selected from the group consisting of alkyl radicals having 1–4 carbon atoms;
$R_2$ is selected from the group consisting of 5,7-, 6,7-, and 7,8-positioned alkoxy groups having 1–4 carbon atoms; $R_3$ is selected from alkoxy groups having 1–4 carbon atoms and $m$ is selected from the group consisting of 1, 2, and 3.

Suitable examples of piperazine compounds include piperazine, N-($\beta$-hydroxyethyl)-piperazine, N-($\gamma$-hydroxypropyl)-piperazine, N-(4-chlorophenyl)-piperazine, N-(2,3,4-trimethoxybenzyl)-piperazine, N-(3,4-dimethoxybenzyl)-piperazine, N-(2,6-dimethylphenylcarbamoylmethyl)-piperazine, and N-(3,4,5-trimethoxyphenylcarbamoylmethyl)-piperazine.

The coumarin compounds according to the present invention are obtained in the different known per se methods, the method chosen depending on the envisaged constitution of the final product.

The simplest method of obtaining the coumarin compounds according to the present invention is to acrylate, optionally in the presence of an acid-binding agent, a coumarin derivative having the formula

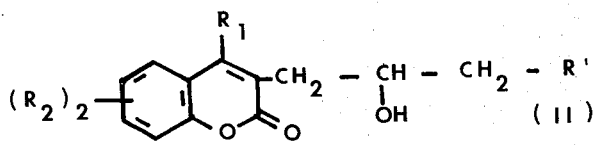

wherein R' is a piperazino base free of hydroxy groups, which is bound via a nitrogen atom, with an alkoxybenzoic acid having the formula

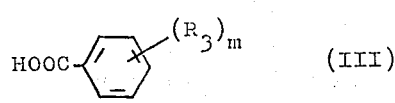

or with a functional derivative thereof and to eliminate by hydrogenation or saponification protective groups in the radical R', if any, which are capable of splitting off and are linked to oxygen or nitrogen atoms.

The 3-$\gamma$-amino-$\beta$-hydroxy-propyl-coumarins required as starting materials for this process are obtained by reacting according to the known methods, for instance analogously to the teachings of British Pat. Nos. 1,067,626 and 1,135,907, the corresponding amines with the 3-$\gamma$-halogen-$\beta$-hydroxypropyl-coumarins, or with the corresponding 3-(2', 3'-epoxypropyl)-coumarins.

Those coumarin derivatives according to the present invention wherein the radical R is bound via the nitrogen atom of a secondary amino group may also be prepared by starting from such coumarin derivatives of the general formula II in which the final secondary amino group contains a protective group capable of splitting off. Thus, after the acylation of the secondary hydroxyl group with an alkoxybenzoic acid or the functional derivative thereof and after the subsequent splitting off of the N-positioned protective group, the secondary alkoxybenzoic acid esters of coumarin of the present invention having the above-mentioned general formula I are obtained, which contain a secondary amino group in the molecule. Particularly suited as protective groups in the above-mentioned sense, which are capable of splitting off are, for instance, the benzyl and benzyloxycarbonyl radicals.

It is advisable to prepare such coumarin derivatives containing a free primary hydroxyl group in the amine radical R by stepwise esterification. In this instance the primary hydroxyl group is at first protected by means of an acyl radical as protective group capable of splitting off, then the secondary hydroxyl group that is still free is reacted with an alkoxybenzoic acid or a functional derivative thereof, and finally the above-mentioned acyl radical is split off again from the primary hydroxyl group.

Another method of preparing the compounds of the present invention which have the general formula I consists in that coumarin derivatives of the general formula

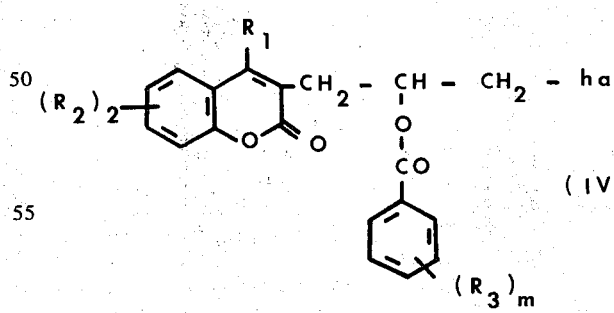

wherein hal stands for a halogen atom are reacted optionally in the presence of an acid-binding agent with an amine of the general formula RH.

Particularly used as amines or bases having the general formula RH are all compounds mentioned above connection with the definition of the radical R.

The starting materials of the general formula IV are obtained by acylating the corresponding 3-γ-halogen-β-hydroxy-propyl-coumarins with an alkoxybenzoic acid of the general formula

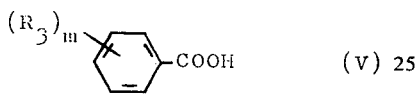

(V)

or with a functional derivative thereof. The reaction may be performed in the presence or absence of an inert solvent and possibly in the presence of an acid-binding agent.

As low-molecular alkyl radicals $R_1$ and alkoxy radicals $R_2$ or $R_3$ are used particularly those having 1–4 carbon atoms.

The coumarin derivatives obtainable under the present invention are valuable pharmaceutics. In particular, they are excellent coronary dilators and, in this respect, superior to other known substances having such properties. Their salts are colorless, crystalline substances that easily dissolve in water.

With respect to the change in the oxygen tension in the coronary veinous blood, the pharmacological investigation of the vasodilator action on the coronary vessels was carried out in dogs according to the methods described by W.K.A. Schaper and his co-workers (see W.K.A. SCHAPER, R. XHONNEUX, and J.M. BOGAARD "Ueber die kontinuierliche Messung des Sauerstoffdruckes im venoesen Coronarblut" (Naunyn-Schmiedeberg's Arch. exp. Path. u. Pharmak. 245, 383–389 (1963)). The test preparations were applied intravenously to the narcotized and spontaneously breathing animals. On these test conditions the dilatation of the coronary arteries caused by the test substances along with the increase in the coronary blood flow led to an increase in the oxygen tension in the coronary veinous blood. This oxygen tension was measured according to polarographic methods by means of a platin electrode of the Gleichmann-Lubbers type (see U. GLEICHMANN and D.W. LUEBBERS "Die Messung des Sauerstoffdruckes in Gasen and Fluessigkeiten mit der Platin-Elektrode unter besonderer Berucksichtigung der Messung im Blut," Pflugers Arch. 271, 431–455 (1960)). The heart rate was continuously measured by electronic methods from systolic peaks of the arterial blood pressure. The arterial blood pressure was measured in the known manner in the femoral artery with the aid of an electromanometer of the Statham-strain-gauge type.

The following table gives the results of the pharmacological investigations which were carried through. The preparations were tested in the form of their respective dihydrochlorides:

| Preparation | LD 50 g./kg. Mouse | Dosage mg./kg. i.v. | Maximal Increase in Oxygen Tension in the Coronary Veinous Blood | | Maximal Change in the Heart Rate | | Maximal Change in the Blood Pressure (systolic/ diastolic) | |
|---|---|---|---|---|---|---|---|---|
| | | | in % | in Mins. | in % | in Mins. | in % | in Mins. |
| 3-[γ-(N-3,4-dimethoxy-benzyl-piperazino)-β-(3,4,5-trimethoxybenzoxy)-propyl]-4-methyl-7,8-dimethoxy-coumarin | | 0.5 | +60 | >25 | −20 | >25 | −57/−66 | >25 |
| 3-[γ-{N-(2,6-dimethyl-anilidocarbonylmethyl)-piperazino}-β-(3,4,5-trimethoxybenzoxy)-propyl]-4-methyl-7,8-dimethoxy-courmarin | i.v.: >0.4 | 0.5 | +36 | >20 | ± 0 | — | ± 0 | — |

In the preparation of dragèes and tablets containing as essential active ingredient the coumarin derivatives of our invention these substances may be admixed with the conventional solid tabletting adjuvants, such as starch, lactose, talc and the like. Any of the tabletting materials and carriers customary in pharmaceutical practice may be employed.

For the preparation of the injection solutions the hydrochlorides of the coumarin derivatives are particularly suited since they have mostly a good water-solubility. Injection solutions of water-insoluble products may of course be prepared in the conventional manner by concurrently using well known suspending agents, emulsifiers and/or solubilizers.

For a better understanding of the nature and the objects of this invention, reference should be made to the accompanying examples which are of an illustrative rather than a limiting nature. Unless otherwise stated, all temperatures given are in degrees Centigrade.

EXAMPLE 1

47.3 g. (0.1 mol) 3-{γ-[4-(4'-chlorophenyl)-piperazine(1)]-β-hydroxypropyl}-4-methyl-7,8-dimethoxy-coumarin are suspended, with the addition of 12.1 g. (0.12 mol) triethylamine, in 800 c.c. anhydrous toluene. Subsequently, a solution consisting of 27.6 g. (0.12 mol) 3,4,5-trimethoxybenzoylchloride in 130 c.c. anhydrous toluene is added dropwise, while stirring at room temperature, and the reaction mixture is heated to 80°. Stirring is continued at this temperature for 10 hours. The toluene solution is sucked off, while hot, from the separated triethylamine hydrochloride and the filtrate is evaporated to dryness in vacuo. The residue is dissolved in ethyl acetate and this solution is washed with an aqueous sodium hydroxide solution and subsequently with water. After drying over potassium carbonate and introduction of gaseous hydrochloric acid into the ethyl acetate solution one obtains the 3-{γ-[4-(4'-chlorophenyl)-piperazino(1)]-β-3,4,5-trimethoxybenzoxypropyl)-4-methyl-7,8-dimethoxy-coumarin dihydrochloride in the form of colorless crystals melting at 155°.

Yield: 58 g. = 79 percent of the theoretical.

The 3-{γ-[4-(4'-chlorophenyl)-piperazino(1)]-β-hydroxypropyl}-4-methyl-7,8-dimethoxy-coumarin required as starting material may be prepared as follows:

31.3 g. (0.1 mol) 3-(γ-chloro-β-hydroxy-propyl)-4-methyl-7,8-dimethoxy-coumarin, prepared according to the method described in British Pat. No. 1,135,907, Example 2, para 2, and 20 g. (0.1 mol) N-4-chlorophenyl-piperazine are dissolved in 300 c.c. chlorobenzene and, after the addition of 12.7 g. (0.12 mol) sodium carbonate, heated while stirring to 120°. Stirring is continued at this temperature for 12 hours and then the reaction mixture is sucked off, while hot. The filtrate is evaporated to dryness in vacuo and, for further purification, the residue thus obtained is recrystallized from ethyl acetate. Obtained is, in the form of colorless crystals, the 3-{γ-[4-(4'-chlorophenylpiperazino(1)]-β-hydroxy-propyl}-4-methyl-7,8-dimethoxycoumarin which has a melting point of 180°.

Yield: 38 g. = 80.3 percent of the theoretical.

Other compounds of the present invention which are prepared according to the above described method, as well as properties thereof, are shown in the following table:

dimethoxycoumarin is obtained in the form of colorless crystals having a melting point of 88°–90°.

Yield: 55 g. = 82 percent of the theoretical.

67.2 g. (0.1 mol) 3-{γ-4-[β-(ethoxycarbonyloxy)-ethyl]-piperazino(1)-β-(3,4,5-trimethoxybenzoxy)-propyl}-4-methyl-7,8-dimethoxy-coumarin are stirred for 4 hours at 70°–80° in 100 c.c. 10% aqueous hydrochloric acid. After cooling down, the limpid solution is rendered alkaline with potassium carbonate, and the precipitated colorless oil is extracted with ethyl acetate. The organic solution is dried over anhydrous sodium sulfate and evaporated to dryness at 40° in the water-jet vacuum. The residue, a colorless oil, is dissolved in anhydrous ether. By adding etheric hydrochloric acid, until congo paper turns blue, the dihydrochloride of 3-[γ-4-(β-hydroxyethyl)-piperazino(1)-β-(3,4,5-trimethoxybenzoxy)-propyl]-4-methyl-7,8-dimethoxy-coumarin is obtained in the form of color-

| $(R_3)_m$ | $(R_2)_2$ | $R_1$ | R | Melting Point: (dihydrochloride) |
|---|---|---|---|---|
| 3,4,5-(OCH$_3$)$_3$ | 7,8-(OCH$_3$)$_2$ | CH$_3$ | 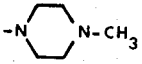 | 160° |
| 3,4,5-(OCH$_3$)$_3$ | 7,8-(OCH$_3$)$_2$ | CH$_3$ | 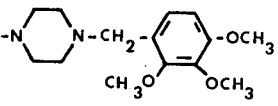 | 208° |
| 3,4,5-(OCH$_3$)$_3$ | 7,8-(OCH$_3$)$_2$ | CH$_3$ | 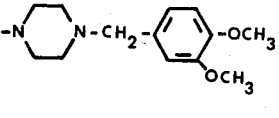 | 240° |
| 3,4,5-(OCH$_3$)$_3$ | 7,8-(OCH$_3$)$_2$ | CH$_3$ | 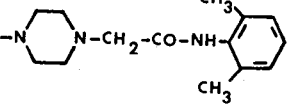 | 161° |
| 3,4,5-(OCH$_3$)$_3$ | 7,8-(OCH$_3$)$_2$ | CH$_3$ | 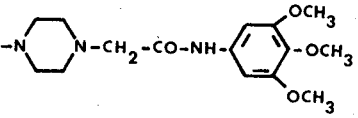 | 165° |

EXAMPLE 2

47.8 g. (0.1 mol) 3-{γ-4-[β-(ethoxycarbonyloxy)-ethyl]-piperazino(1)-β-hydroxy-propyl}-4-methyl-7,8-dimethoxycoumarin are dissolved in 200 c.c. anhydrous chloroform and 10.1 g. (0.1 mol) triethylamine are added. Within one hour, a solution of 23 g. (0.1 mol) 3,4,5-trimethoxybenzoylchloride in 100 c.c. anhydrous chloroform is added dropwise with stirring at room temperature. After the decay of the exothermic reaction, the reaction mixture is stirred for 2 hours at 40°–50° and worked up in a conventional manner. The 3-{γ-4-[β-(ethoxycarbonyloxy)-ethyl]-piperazino(1)-β-(3,4,5-trimethoxybenzoxy)-propyl}-4-methyl-7,8-less crystals melting at 155° with decomposition.

Yield: 45 g. = 67 percent of the theoretical.

The 3-{γ-4-[β-(ethoxycarbonyloxy)-ethyl]-piperazino(1)-β-hydroxy-propyl}-4-methyl-7,8-dimethoxy-coumarin which is used as starting material can be prepared as follows:

40.6 g. (0.1 mol) 3-[γ-4-(β-hydroxyethyl)-piperazino(1)-β-hydroxy-propyl]-4-methyl-7,8-dimethoxy-coumarin (prepared according to the technique described in British Pat. No. 1,135,907, Example 2, paragraph 2 and 3) are dissolved in 200 c.c. anhydrous chloroform and 10.1 g. (0.1 mol) triethylamine are added. A solution of 10.8 g. (0.1 mol) ethyl chloroformate in 100 c.c. anhydrous chloroform is added dropwise within 1 hour at room temperature. The reaction solution is stirred for 5 hours at room temperature, washed several times with water, with a 10% aqueous sodium bicarbonate solution and again with water. After having been dried over anhydrous sodium sulfate, the solvent is distilled off at 40° in a water-jet vacuum. The residue is recrystallized from isopropanol. Thus, 3-{γ-4-[β-(ethoxycarbonyloxy)-ethyl]-piperazino(1)-

β-hydroxy-propyl}-4-methyl-7,8-dimethoxycoumarin is obtained in the form of colorless crystals, having a melting point of 118°.

Yield: 40 g. = 83.5 percent of the theoretical.

The 3-{γ-4-[β-hydroxyethyl]-piperazino(1)-β-(3,4,5-trimethoxybenzoxy)-propyl}-4-methyl-7,8-dimethoxy-coumarin can also be prepared by reacting, at 120°, and with the concurrent use of triethylamine 3-[γ-chloro-β(3,4,5-trimethoxybenzoxy)-propyl]-4-methyl-7,8-dimethoxy-coumarin with N-β-hydroxyethyl-piperazine in chlorobenzene.

What is claimed is:

1. A coumarin compound having the structural formula

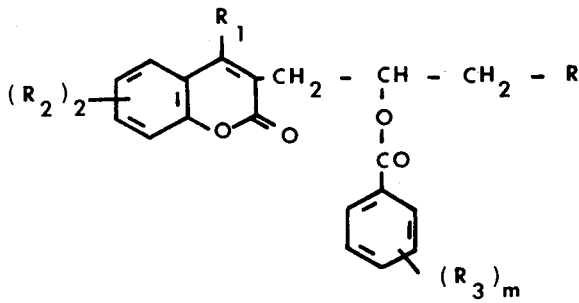

or the hydrochloric acid addition salts thereof, wherein R is selected from the group consisting of piperazino, N-(β-hydroxyethyl)-piperazino, N-(γ-hydroxypropyl)-piperazino, N-(4-chlorophenyl)-piperazino, N-(2,3,4-trimethoxybenzyl)-piperazino, N-(3,4-dimethoxybenzyl)-piperazino, N-(2,6-dimethylphenyl-carbamoylmethyl)-piperazino, and N-(3,4,5-trimethoxyphenylcarbamoylmethyl)-piperazino and is bound via a nitrogen atom; $R_1$ is selected from the group consisting of alkyl groups having 1–4 carbon atoms; $R_2$ is selected from the group consisting of 5,7-, 6,7-, and 7,8-positioned alkoxy groups having 1–4 carbon atoms; $R_3$ is selected from alkoxy groups having 1–4 carbon atoms; and $m$ is selected from the group consisting of 1, 2, and 3.

2. A coumarin compound according to claim 1, wherein R is N-(β-hydroxyethyl)-piperazino.

3. A coumarin compound according to claim 1, wherein R is N-(γ-hydroxypropyl)-piperazino.

4. A coumarin compound according to claim 1, wherein R is N-(p-chlorophenyl)-piperazino.

5. A coumarin compound according to claim 1, wherein R is N-(2,3,4-trimethoxybenzyl)-piperazino.

6. A coumarin compound according to claim 1, wherein R is N-(2,6-dimethylphenyl-carbamoylmethyl)-piperazino.

* * * * *